(12) United States Patent
Sama

(10) Patent No.: US 11,745,009 B2
(45) Date of Patent: Sep. 5, 2023

(54) ORAL MUSCLE TRAINING

(71) Applicant: Signifier Medical Technologies Limited, London (GB)

(72) Inventor: Anshul Sama, Nottingham (GB)

(73) Assignee: Signifier Medical Technologies Limited, London (GB)

( * ) Notice: Subject to any disclaimer, the term of this patent is extended or adjusted under 35 U.S.C. 154(b) by 0 days.

(21) Appl. No.: 16/655,375

(22) Filed: Oct. 17, 2019

(65) Prior Publication Data

US 2020/0121921 A1 Apr. 23, 2020

(30) Foreign Application Priority Data

Oct. 17, 2018 (GB) ..................................... 1816882

(51) Int. Cl.
*A61N 1/36* (2006.01)
*A61N 1/05* (2006.01)

(52) U.S. Cl.
CPC ........... *A61N 1/0548* (2013.01); *A61N 1/057* (2013.01); *A61N 1/3603* (2017.08)

(58) Field of Classification Search
CPC .... A61N 1/0548; A61N 1/3603; A61N 1/057; A61N 1/36014; A61N 1/0452; A61N 1/36003
See application file for complete search history.

(56) References Cited

U.S. PATENT DOCUMENTS 5,190,053 A * 3/1993 Meer .................... A61N 1/0548
600/529
5,265,624 A 11/1993 Bowman
5,284,161 A 2/1994 Karell
5,490,520 A 2/1996 Schaefer et al.
6,212,435 B1 4/2001 Lattner et al.
(Continued)

FOREIGN PATENT DOCUMENTS

CN 101590302 12/2009
CN 101596340 A 12/2009
(Continued)

OTHER PUBLICATIONS

Joerg Steier, Chest, Original Research, Sleep Disorders; Continuous Transcutaneous Submental Electrical Stimulation in Obstructive Sleep Apnea.

*Primary Examiner* — Ankit D Tejani
*Assistant Examiner* — Joshua Brendon Solomon
(74) *Attorney, Agent, or Firm* — Shay Glenn LLP

(57) ABSTRACT

Apparatus (100) for training oral muscle tone, the apparatus (100) includes a mouthpiece (103) having first electrode means (132a, 132b, 133a, 133b) associated with the mouthpiece (103) and second electrode means (152a, 152b) for location exterior of the mouth of the user, electrical circuitry operatively connected to the first (132a, 132b, 133a, 133b) and second (152a, 152b) electrode means, wherein the apparatus (100) is configured to provide, in use, via the first (132a, 132b, 133a, 133b) and/or second (152a, 152b) electrode means electrical stimulation to one or more oral muscles to increase resting muscle tone and/or muscle tone during sleep, the second electrode means (152a, 152b) including a first and second electrode (152a, 152b), the first and second electrodes (152a, 152b) of the second electrode means being located or locatable lateral of a midline of the face of the user.

21 Claims, 5 Drawing Sheets

(56) References Cited

U.S. PATENT DOCUMENTS

| | | |
|---|---|---|
| 8,744,589 B2 | 6/2014 | Bolea et al. |
| 9,717,904 B2 | 8/2017 | Simon et al. |
| 9,833,613 B2 | 12/2017 | Sama |
| 10,058,701 B2 | 8/2018 | Sama |
| 10,195,427 B2* | 2/2019 | Kent .................... A61B 5/0826 |
| 10,463,850 B2 | 11/2019 | Fisk et al. |
| 10,561,836 B2 | 2/2020 | Sama |
| 10,596,366 B2 | 3/2020 | Sama |
| 10,646,319 B2 | 5/2020 | Johansson et al. |
| 2003/0003422 A1 | 1/2003 | Pasquantonio et al. |
| 2005/0038485 A1 | 2/2005 | Ludwig et al. |
| 2007/0123950 A1* | 5/2007 | Ludlow ............... A61N 1/36007 |
| | | 607/42 |
| 2007/0173893 A1 | 7/2007 | Pitts |
| 2009/0048647 A1 | 2/2009 | Tingey |
| 2009/0210032 A1 | 8/2009 | Beiski et al. |
| 2010/0087893 A1 | 4/2010 | Pasquet |
| 2010/0087896 A1 | 4/2010 | McCreery |
| 2010/0204747 A1 | 8/2010 | Lindquist et al. |
| 2011/0112601 A1 | 5/2011 | Meadows |
| 2011/0155143 A1 | 6/2011 | Shantha |
| 2014/0093832 A1 | 4/2014 | Nemeh et al. |
| 2014/0135868 A1 | 5/2014 | Bashyam |
| 2014/0277323 A1 | 9/2014 | Tingey |
| 2015/0093716 A1 | 4/2015 | Fulton, III |
| 2015/0142120 A1* | 5/2015 | Papay .................. A61N 1/0456 |
| | | 623/17.17 |
| 2015/0190630 A1 | 7/2015 | Kent et al. |
| 2016/0106976 A1* | 4/2016 | Kucklick ............. A61N 1/0548 |
| | | 607/42 |
| 2016/0158093 A1 | 6/2016 | Amblard et al. |
| 2016/0317803 A1* | 11/2016 | Sama .................... A61N 1/3601 |
| 2017/0143257 A1 | 5/2017 | Kent et al. |
| 2017/0143259 A1 | 5/2017 | Kent et al. |
| 2017/0143960 A1 | 5/2017 | Kent et al. |
| 2017/0224987 A1 | 8/2017 | Kent et al. |
| 2018/0036531 A1 | 2/2018 | Schwarz et al. |
| 2020/0121924 A1 | 4/2020 | Sama |
| 2020/0121984 A1 | 4/2020 | Sama |
| 2020/0164205 A1 | 5/2020 | Sama |
| 2020/0346016 A1 | 11/2020 | Caparso et al. |

FOREIGN PATENT DOCUMENTS

| | | |
|---|---|---|
| CN | 102548610 A | 7/2012 |
| EP | 0122102 | 10/1984 |
| EP | 1365832 | 10/2019 |
| GB | 1038829 | 8/1966 |
| JP | 2000511087 A | 8/2000 |
| JP | 2014 158607 | 9/2014 |
| JP | 2015093133 A | 5/2015 |
| RU | 2223798 | 2/2004 |
| RU | 2457006 | 7/2012 |
| TW | 615168 | 2/2018 |
| TW | 201505682 | 2/2018 |
| TW | I615168 B | 2/2018 |
| WO | 1992/015364 | 9/1992 |
| WO | 9215364 | 9/1992 |
| WO | 1997018854 | 5/1997 |
| WO | 2000029063 | 5/2000 |
| WO | 2002/066111 | 1/2002 |
| WO | 02066111 | 8/2002 |
| WO | WO2005/072821 A1 | 8/2005 |
| WO | WO2006/001644 A1 | 1/2006 |
| WO | 2008/100779 | 8/2008 |
| WO | WO2009/127947 A2 | 10/2009 |
| WO | WO2013/144710 A1 | 10/2013 |
| WO | WO2020/081831 A1 | 4/2020 |
| WO | WO2022/118028 A1 | 6/2022 |

* cited by examiner

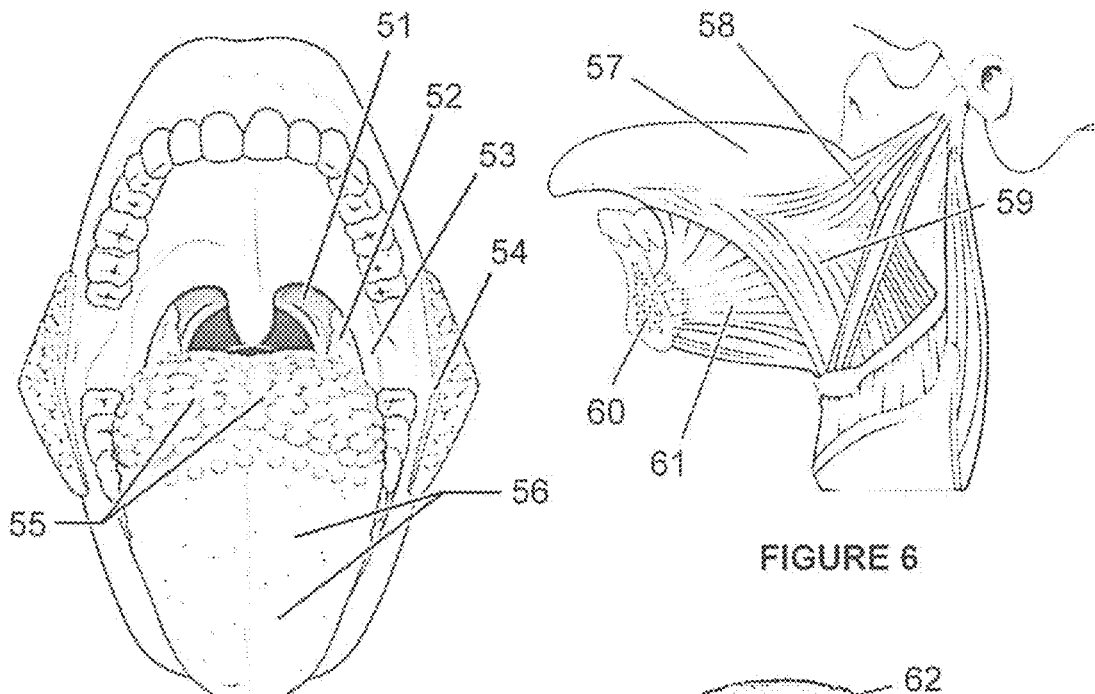
FIGURE 5
FIGURE 6
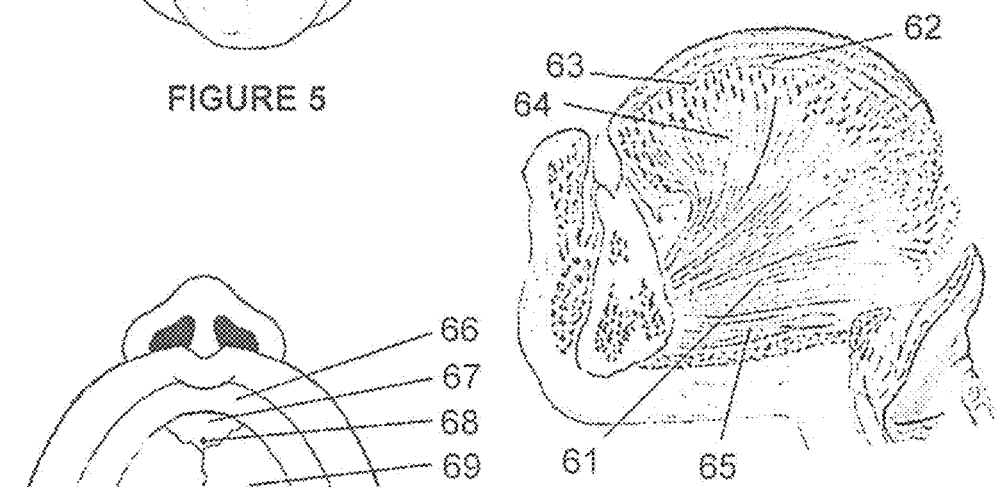
FIGURE 7
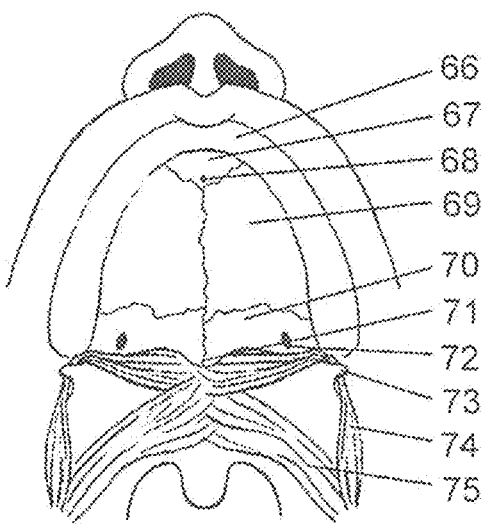
FIGURE 8
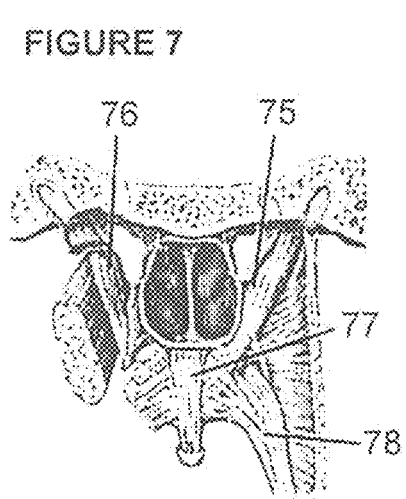
FIGURE 9

| Electrode | 1st | Direction | 2nd |
|---|---|---|---|
| | 132a, 132a' | ←——→ | 132b, 132b' |
| | 133a, 133a' | ←——→ | 133b, 133b' |
| | 152a | ←——→ | 152b |

FIGURE 10A – Lateral Stimulation

| Electrode | 1st | Direction | 2nd |
|---|---|---|---|
| | 132a, 132a' | ↕ | 132b, 132b' |
| | 133a, 133a' | ↕ | 133b, 133b' |
| | 152a | ↕ | 152b |

FIGURE 10B – Vertical Stimulation

| Electrode | 1st | Direction | 2nd |
|---|---|---|---|
| | 132a, 132a' | ←——→ | 132b, 132b' |
| | 133a, 133a' | ↘↗ | 133b, 133b' |
| | 152a | ↗↘ | 152b |

FIGURE 10C – Diagonal/lateral Stimulation

| Electrode | 1st | Direction | 2nd |
|---|---|---|---|
| | 132a, 132a' | ↘↗ | 132b, 132b' |
| | 133a, 133a' | ↗↘ | 133b, 133b' |
| | 152a | ←——→ | 152b |

FIGURE 10D – Lateral/diagonal Stimulation

ORAL MUSCLE TRAINING

This invention relates generally to oral muscle training, particularly to oral muscle training devices, methods, systems and control software. More specifically, although not exclusively, this invention relates to the training of muscles of the mouth for the treatment of sleep disordered breathing.

Snoring and sleep apnoea are considered as part of a range of conditions often termed as sleep disordered breathing (SDB), with symptoms relating to disordered breathing patterns during sleep. SDBs are not only a nuisance, but they can also result in health problems, for example frequent waking from sleep, light sleeping, strain on the heart, low oxygen levels in the blood, headaches and fatigue. Moreover, a partner of a person exhibiting SDB may also suffer from fatigue etc due to the SDB symptoms.

The breathing passage of humans between the throat, back of the nose and mouth, to the level of the larynx, is a collapsible tube. It has been observed that collapse of the breathing passage occurs at a positive airway pressure in individuals who snore and/or suffer from sleep apnoea syndrome and at a negative airway pressure in individuals who do not.

In an effort to address this phenomenon, treatments have been developed which include using a continuous positive airway pressure device to keep the breathing passage open or wearing a mandibular advancement device to hold the jaw and tongue forward in order to increase the space at the back of the throat.

These devices can cause discomfort such as a dry throat, they address the symptoms only temporarily, rather than addressing the underlying cause, and they must be used during sleep on an ongoing basis. As a result, users find it difficult to fall asleep or remain asleep and compliance is therefore low. Therefore, it is desirable to provide a treatment that does not require the regular use of such devices during sleep and that addresses the underlying cause for the condition.

Recent research studies have shown that implanting electrical nerve stimulators into the tongue and diaphragm are effective in the treatment of obstructive sleep apnoea. This involves intrusive surgery to implant sensors and electrodes on nerves in these areas. The device identifies an episode of obstruction using the sensors and stimulates the tongue nerve to cause contraction to relieve the obstructive event. As with pacemakers, this approach leads to maintenance and other complications, such as battery replacement, risks associated with electrical fields and issues related to external security detection devices. In addition, stimulation only occurs during an obstructive episode during sleep; it does not address the underlying cause of the condition.

In our earlier patent U.S. Pat. No. 9,833,613, we disclose a device for the treatment of SDB wherein a user is able to train muscles of the mouth to improve muscle tone and thereby stop, or at least inhibit, SDB events. The user will typically apply the device whilst in an awake state to improve muscle tone. In one embodiment the device has a mouthpiece for location between the upper and lower mandibular arches and a pair of flanges for engaging the upper or dorsal surface of the tongue and a pair of flanges for engaging the sublingual surface of the tongue, each of the flanges including an electrode. Energising the device causes an electric current to be applied to the tongue between the sublingual and dorsal surfaces to target the genioglossus muscle and thereby improve tongue muscle tone.

Whilst the device disclosed in our previous patent is clinically proven to reduce SDB events, further or different methodologies can be applied to further improve oral muscle tone of a user.

It is therefore a first non-exclusive object of the invention to provide a treatment system, preferably to be used in an awake state, that provides a sustainable reduction in disordered breathing patterns during sleep. It is a further, more general object of the invention to provide a treatment system and device that is more effective in at least one respect than existing systems and devices for the treatment of SDBs.

Accordingly, a first aspect of the invention provides apparatus for training oral muscle tone, the apparatus comprising a mouthpiece having first electrode means or a first electrode set associated with the mouthpiece and second electrode means or a second electrode set for location exterior of the mouth of the user, electrical circuitry operatively connected to the first and second electrode means (or first and second electrode sets), wherein the apparatus is configured to provide, in use, via the first and second electrode means (or first and second electrode sets) electrical stimulation to one or more oral and/or floor of mouth muscles to increase resting muscle tone and/or muscle tone during sleep, the second electrode means (or second electrode set) comprising a first and second electrode, the first and second electrodes of the second electrode means (or second electrode set) being located or locatable lateral of a midline of the face of the user.

As is known, the midline of the face is a nominal line which extends from the top of the forehead, along the bridge of the nose along the centre of the philtral ridge via the inferior convexity of the cupids bow across the lips and along the centre of the chin.

The first electrode means (or first electrode set) may comprise first and second electrodes. The first and second electrodes of the first electrode means (or first electrode set) may be located or locatable lateral of a midline of the face and lateral of the external floor of mouth of the user. The first electrode means (or first electrode set) may be arranged or configured, in use, to bear against a sublingual surface of the tongue.

By locating the first and second electrode of the second electrode means (or second electrode set) transverse or lateral of the midline it is possible to apply an electric current to muscles other than those on the midline of the user. In particular, locating the first and second electrodes of the second electrode means (or second electrode set) lateral to the midline allows the apparatus to stimulate the mylohyoid, geniohyoid and anterior belly of digastric muscles. Moreover, it also allows the apparatus to selectively stimulate muscles at different sides of the mouth to a different amount, and or to provide a varied stimulation profile to different sides of the muscles of the mouth. For example, it is possible for the first and second electrodes of the second electrode means (or second electrode set) to apply a lateral current from one side of the midline to the other side of the midline of the user. It is also possible for the first and second electrodes of the second electrode means (or second electrode set) to apply a vertical current, for example in association with the first electrode means (or first electrode set). Accordingly, the first and second electrodes of the second electrode means (or second electrode set) may be arranged or configured, in use, to apply an electrical current laterally of the midline of the user and/or the first and second electrodes of the second electrode means (or each of them) may be arranged or configured, in use, to apply an electrical current vertically or diagonally.

When a person is awake, the collapsible segment of the breathing passage is kept open due to the tone of the muscles that control this area. When a person is asleep, this muscle tone reduces significantly. Evidence has shown that this reduction of muscle tone is significantly greater in patients who suffer from obstructive sleep apnoea, less so in those who snore and notably less in individuals who suffer from neither of these disorders.

Research has demonstrated that increasing the pharyngeal muscle activity or tone reduces the collapsibility of the airway and the present invention is based on the realisation that electrical stimulation, particularly neuromuscular electrical stimulation, can be used to stimulate the muscles of the tongue and/or palate and/or the sensory nerves to improve muscle power and tone recovery.

In embodiments, the first and second electrodes of the second electrode means (or second electrode set) may comprise connecting means or a connector configured to connect or link, e.g. physically connect or link, the second electrode means (or second electrode set) to the mouthpiece. The connecting means may comprise one or more arms or leads or wires, e.g. a pair of arms or leads or wires. A pair of arms or leads or wires may be arranged or configured to link a respective electrode of the second electrode means (or second electrode set) to the mouthpiece. For example, the first electrode may be linked to the mouthpiece by a first arm or lead or wire and the second electrode may be linked to the mouthpiece by a second arm or lead or wire. The connector or connecting means may further comprise the electrical circuitry to operatively electrically connect the first and second electrode of the second electrode means to the mouthpiece and/or a power supply.

In embodiments, the connector or connecting means comprises two or more, e.g. a pair of, arms or leads or wires. In an embodiment the two or more arms leads or wires are of the same length. For example, each of a pair of arms or leads or wires that connect or link a respective electrode of the second electrode means may be the same length as one another.

Advantageously, the provision of a pair of arms or leads or wires that are the same length for connecting the first and second electrode of the second electrode means (or second electrode set) to the mouthpiece enables the first and second electrode of the second electrode means (or second electrode set) to be located or locatable lateral of a midline of the face of the user, e.g. symmetrically and lateral of a midline of the face of the user.

The apparatus is preferably configured to provide a current, for example an electric current or impulse current, which may be selected from one or more of a Russian current, interferential current, premodulated current, DC electric current, biphasic electric current or impulse current. Other current forms may be used. We prefer to apply the smallest potential difference and drive the lowest possible current to effect the required stimulation (and/or muscle contraction). Electrical stimulation may be used in combination with optical, thermal and/or vibratory stimuli to reduce the current required.

Another aspect of the invention provides an electrical stimulation apparatus for training one or more oral muscles, for example a trans mucosal neuromuscular electrical stimulation device, the device comprising a mouthpiece, first electrode means (or first electrode set) associated with the mouthpiece, second electrode means (or second electrode set) comprising two or more electrodes for securement to the exterior of the user's head, for example the user's face or external floor of mouth and electrical circuitry operatively connected to each of the first and second electrode means (or first and second electrode set), wherein the apparatus or electrical circuitry is configured to provide, in use, via the second and/or first electrode means (or second and/or first electrode set) a current, for example a biphasic electric current, for example biphasic electric impulse current.

By providing a current, e.g. a biphasic electric current, particularly a biphasic electric impulse current, tongue, floor of mouth and/or palate muscles contributing to the collapsibility of the airway can be stimulated along with the sensory nerves to increase resting muscle tone and muscle tone during sleep.

The current is preferably a biphasic symmetrical current, but it may additionally or alternatively be a biphasic asymmetrical current that may either be balanced or unbalanced. The device or electrical circuitry may be configured to provide, in use, via the electrode means an electric current with a frequency of up to 150 Hz, say between 1, 2, 3, 4 or 5 Hz and 150 Hz.

Another aspect of the invention provides an electrical stimulation apparatus for training one or more oral muscles, for example a trans mucosal neuromuscular electrical stimulation device, the device comprising a mouthpiece, first electrode means (or first electrode set) associated with the mouthpiece, second electrode means (or second electrode set) comprising a pair of electrodes for location on the exterior of a user's head, for example the user's face or external floor of mouth, and electrical circuitry operatively connected to the first and second electrode means, wherein the device or electrical circuitry is configured to provide, in use, via the first and second electrode means an electric current with a frequency of between 1 and 150 Hz.

The electric current may comprise a frequency of between say 1 to 10 Hz, say 1 to 9, 8, 7, 6, 5 Hz or between 10 and 140 Hz, for example between 15 and 130 Hz, preferably between 20 and 120 Hz. Preferably, the electric current comprises a frequency of between 20 and 50 Hz and/or between 50 and 120 Hz.

The electric current applied by the first electrode means and second electrode means may be the same or different. In one embodiment, the second electrode means may generate a larger current than the first electrode means.

The apparatus or electrical circuitry may be configured to provide two or more currents, for example a first current and/or a second current and/or a third current, which second current may be different from and/or configurable or settable independently from the first current and/or third current. At least one, e.g. all, of the first and/or second current and/or third current may comprise a biphasic current or a monophasic current, each of which is preferably symmetrical, but may be asymmetrical and either balanced or unbalanced. At least one of the first and/or second current and/or a third current may comprise a frequency of up to 150 Hz, say between 5 and 150 Hz, for example between 1 and 150 Hz or between 10 and 140 Hz, e.g. between 15 and 130 Hz, preferably between 20 and 120 Hz. In some embodiments, one or the currents may comprise a frequency of between 1 and 50 Hz (e.g. between 1 and 5 Hz), for example 5 to 20 Hz or 20 and 50 Hz and/or the other current may comprise a frequency of between 1 and 120 Hz.

The inventors believe that the application of an electric current in one or each of these two frequency ranges is particularly suited to targeting palate and tongue muscles and muscles of the floor of the mouth contributing to the collapsibility of the airway.

The device or electrical circuitry may be configured to provide, in use, the or at least one or each electrical current to one or more oral muscles, such as palate and/or tongue muscles and/or the muscles of the floor of the mouth, for example through the floor of the mouth, the lining of the mouth, e.g. the oral mucosa, such as to increase resting muscle tone and/or muscle tone during sleep. In some embodiments, the apparatus is configured to provide, in use, the electrical current, e.g. the first electrical current, to one or more muscles of the floor of the mouth such as one or more of the mylohyoid, geniohyoid and/or anterior belly of digastric muscles. Additionally or alternatively, the apparatus may be configured to provide, in use, the electrical current, e.g. a first or second electrical current, to one or more tongue muscles, e.g. via the dorsal tongue surface. Additionally or alternatively, the device may be configured to provide, in use, the electrical current, e.g. the first or second electrical current, to one or more tongue muscles e.g. genioglossus via the sublingual surface (underside) of the tongue. In a particular embodiment the first electrode means comprises first and second electrodes. The first and second electrodes of the first electrode means may bear against the sublingual surface of the tongue.

Third electrode means (or third electrode set) may be provided. The third electrode means may be associated with the mouthpiece. The mouthpiece may comprise third electrode means. The third electrode means may comprise a first and second electrode. The third electrode means may, in use, bear against the dorsal surface of the tongue.

The first, second and/or third electrode means may be operable such that the applied electrical current causes stimulation to be applied laterally between the electrodes of the first electrode means, or between the electrodes of the second electrode means, or between the electrodes of the third electrode means. Additionally or alternatively, the first, second and third electrode means may be operable such that an electric current applied to cause stimulation to be effected vertically between the electrodes of the first electrode means and the second electrode means, and/or between the electrodes of the second electrode means and the third electrode means, and/or between the electrodes of the first electrode means and the third electrode means. The first, second and/or third electrode means may be operable such that an electric current is applied to cause stimulation to be effected diagonally, say from and/or between the first electrode means to or from the second and/or third electrode means.

A controller may be present. The controller may be arranged to selectively energise the electrodes of the second electrode means laterally with a current having a first set of parameters (mode 1). This mode 1 may be stopped or continued whilst the controller is arranged to selectively energise the second electrode means and say third electrode means vertically with a second set of parameters (mode 2). Additionally or alternatively, the controller may be arranged to energise electrodes of the first electrode means and the second electrode means vertically with a third set of parameters (mode 3). Mode 3 may be arrested or continued whilst the controller is arranged to energise the third electrode means laterally with a fourth set of parameters (mode 4). As will be appreciated, different and further modes may be provided based on the combination of the three separately controllable electrode means, for example to generate lateral or vertical stimulation, or both lateral and vertical stimulation of the various muscle groups.

Preferably, all electrodes of the first and/or second, and/or third electrode means are located such that they do not intersect with the midline of the face of the user during use.

In embodiments, the mouthpiece may comprise one or more arms and/or one or more appendages or flanges which may extend from the one or more arms, e.g. for contacting one or more oral muscles. At least one arm and/or at least one appendage or flange may be flat or planar, for example with major surfaces. Optionally, the mouthpiece may comprise a pair of arms each of which may comprise one or more appendages or flanges. In some embodiments, the mouthpiece comprise a pair of arms that may extend at least partially alongside each other and/or at an angle relative to one another and/or parallel to each other. For example, the mouthpiece may comprise a pair of arms joined together at one end and diverging from one another, for example in a substantially V-shape or U-shape or horseshoe shape.

The one or more appendages or flanges may extend inwardly of the pair of arms, e.g. from one arm and toward the other arm. In some embodiments, each arm comprises at least one appendage or flange, for example opposite one another and/or extending toward one another. In embodiments, each arm comprises two or more appendages or flanges, for example an appendage or flange extending from a free end of each arm and/or an appendage or flange extending from an intermediate portion of each arm.

At least one appendage or flange may be curved, e.g. a flat curved shape or member, and/or extend upwardly or downwardly or out of the plane of the mouthpiece or at least one arm thereof. At least one appendage or flange may be shaped to cooperate or approximate or accommodate a tongue surface, for example a dorsal tongue surface or a sublingual tongue surface. In embodiments, the mouthpiece comprises at least one appendage or flange that is shaped to cooperate or approximate or accommodate a dorsal tongue surface and at least one appendage or flange that is shaped to cooperate or approximate or accommodate a sublingual tongue surface. In embodiments having a pair of arms, each arm may comprise an appendage or flange shaped to cooperate or approximate or accommodate a dorsal tongue surface and an appendage or flange that is shaped to cooperate or approximate or accommodate a sublingual tongue surface.

At least one of the appendages or flanges may comprise one or more electrodes or series thereof. At least one electrode or series of electrodes may be adjacent and/or associated with and/or exposed at a surface, e.g. a major surface, of the at least one appendage or flange. In embodiments, at least one of the appendages or flanges comprises electrodes associated with each of its major surfaces. The electrodes associated with one of the major surfaces may be isolated and/or controllable independently from another or the other major surface thereof. Additionally or alternatively, the electrodes of or associated with one appendage or flange may be isolated and/or controllable independently from at least one other appendage or flange.

In embodiments, the mouthpiece may comprise a pair of arms joined together at one end and diverging from one another to provide a substantially horseshoe shape with one or more flanges extending inwardly from at least one arm, the or each flange comprising electrode means. The mouthpiece may comprise a pair of flanges each extending inwardly from a respective arm, which flanges are shaped to accommodate a dorsal tongue surface. The mouthpiece may comprises a pair of flanges each extending inwardly from a respective arm, which flanges are shaped to accommodate a sublingual tongue surface. Each of the pair of flanges may be shaped to accommodate a dorsal tongue surface extends from at or adjacent a free end of the arm and/or each of the pair of flanges may be shaped to accommodate a sublingual tongue surface extends from an intermediate portion of the arm.

Another aspect of the invention provides an electrical stimulation apparatus for training one or more oral muscles, for example a trans mucosal neuromuscular electrical stimulation device, the device comprising a mouthpiece, first electrode means (or first electrode set) associated with the mouthpiece, second external electrode means (or second electrode set) and electrical circuitry operatively connected to the first and second electrode means, wherein the mouthpiece comprises a pair of arms joined together at one end and diverging from one another with one or more flanges extending inwardly from at least one arm, the or each flange including at least part of the first electrode means (or first electrode set) associated therewith for providing electrical stimulation to one or more oral muscles and wherein the second electrode means (or second electrode set) are for location lateral of a midline of the user.

Yet another aspect of the invention provides an electrical stimulation apparatus comprising an external electrode means (or external electrode set) and a mouthpiece for training one or more oral or floor of mouth muscles, for example a trans mucosal neuromuscular electrical stimulation mouthpiece, the mouthpiece comprising a pair of arms joined together at one end and diverging from one another with one or more flanges extending inwardly from at least one arm, wherein the or each flange includes electrode means (or electrode set) associated therewith for providing electrical stimulation to one or more oral muscles, the external electrode means (or external electrode set) comprising a first and second electrode for locating on either side of the midline of the external floor of the mouth of a user.

The mouthpiece may comprise a gripping base, which may comprise an enlarged end, e.g. an enlarged free end, which may be connected or secured to, e.g. formed integrally with, the mouthpiece or a body or one or more or each arm thereof, for example by a necked portion.

The or each electrode means preferably comprises at least one anode and at least one cathode, for example two or more anodes and/or two or more cathodes, e.g. a plurality of anodes and a plurality of cathodes. At least part of the electrode means, for example one or more or each or all of the electrodes, may be mounted to or on or within and/or at least partially housed or contained within the mouthpiece. In some embodiments, the mouthpiece comprises a shield or shield means, for example on one side of the electrode means, e.g. for inhibiting or preventing the electrical stimulation or current from being applied or provided by or at or from one side of the mouthpiece. Suitable materials for the shield or shield means will be apparent to those skilled in the art.

In embodiments, the first and/or second and/or third electrode means is configured or operable to provide or apply, e.g. selectively, the electrical stimulation or current at or from at least one or each or both sides of the body to which it is or they are secured (or located), for example by including the or a shielding means or shield between a first set or series of electrode means or electrodes and a second set or series of electrode means or electrodes. In some embodiments, the first electrical current is provided or stimulation applied at or from a first side, e.g. major side, of the mouthpiece and/or by the first set or series of electrode means or electrodes. Additionally or alternatively, the second electrical current may be provided or stimulation applied at or from a second side, e.g. major side, of the mouthpiece and/or by the second set or series of electrode means or electrodes. In other embodiments, the first and second electrical currents may be provided or stimulation applied from at least one or each or both sides.

The mouthpiece may be insertable into the mouth and held in place, e.g. manually. The mouthpiece may be at least partially flattened and/or substantially flat and/or paddle-shaped, for example with at least one flat and/or major surface, preferably two flat major surfaces. In some embodiments, the device may include a handle to which the mouthpiece may be connected or mounted or attached, for example rigidly and/or releasably, e.g. to enable the mouthpiece to be inserted and/or held, in use, within one or more locations or positions and/or orientations within the mouth. In some embodiments, the mouthpiece is free of any mounting means for mounting or securing it to or in or within the mouth of a user. Electrodes on the mouthpiece may protrude proud of the adjacent parts of the mouthpiece. In so doing a robust connection is made to the facing surface of the mouth.

In embodiments, the mouthpiece may include a mounting means. The mounting means may be for mounting the mouthpiece to an upper part or portion of the mouth, for example such that he mouthpiece or the or a first side or surface thereof is or may be in contact with and/or adjacent one or more palate muscles and/or the roof of the mouth and/or the mouthpiece or the or a second side or surface thereof is or may be in contact with and/or adjacent one or more tongue muscles, for example a dorsal tongue surface. Additionally or alternatively, the mounting means may be for mounting the mouthpiece to a lower part or portion of the mouth, for example such that the mouthpiece or the or a first side or surface thereof is or may be in contact with and/or adjacent one or more tongue muscles, for example a sub-lingual tongue surface. In embodiments, the device comprises a first mouthpiece with mounting means for mounting it to an upper part or portion of the mouth and a second mouthpiece for mounting it to a lower part or portion of the mouth.

The apparatus may comprise a controller, for example an input means or activator, which may include one or more input devices, buttons and/or push buttons and/or switches and/or dials or the like, e.g. for enabling or activating or initiating the electrical stimulation or current. The device or handle may comprise a power source and/or a cable connectable to a power source. In some embodiments, the device comprises a main body that includes or incorporates or provides the handle and/or which includes or houses the power source, which may comprise a rechargeable power source or one or more batteries that may be rechargeable, and/or which can either include the cable or be operatively, e.g. inductively, connectable to a charging station that includes or incorporates the cable, for example to enable the power source to be recharged. The device may include the or be connectable to a charging station.

In some embodiments, the device comprises an adjustment means or adjuster, e.g. a frequency adjustment means or adjuster, for adjusting the frequency of the current or of the first and/or second currents, for example a respective first and second current frequency adjustment means or adjuster for adjusting the frequency of the current, e.g. between one of the aforementioned ranges. In embodiments, the adjustment means or adjuster is a step-wise adjustment means or adjuster and/or is configured to enable a user to select from one of two or more, e.g. three, four or five, predetermined frequency settings. The device may be operable or configured to provide the first and second currents simultaneously and/or concurrently and/or in parallel. Additionally or alternatively, the device may be operable or configured to provide the first and second currents in series and/or in sequence and/or in succession. Additionally or alternatively, a thermal, vibratory or optical stimulus can be applied, for example from thermal, optical, or vibratory emission means or emitter.

In other embodiments the controller may be controlled by instructions received from a remote device, for example a remote computing device, such as a smartphone, personal computer, tablet computer and so on. The instructions may be provided via wired or wireless connection. For example, instructions may be provided via Bluetooth® or other wireless protocols. The wired connection may be via a USB, USB-C, MicroUSB, FireWire®, magnetic connectors or other wired interface. The instructions may be provided by software held on a remote computing device. In one embodiment, the instructions may be provided from an APP provided on a personal computing device, for example a smart phone or tablet.

The current or at least one, e.g. both, of the first and/or second current may comprise an impulse current. The pulse duration of the or each impulse current may be between 50 and 1000 μs, for example between 100 and 900 μs, e.g. between 150 and 800 μs, preferably between 200 and 700 μs. Preferably, the or a further adjustment means or adjuster, e.g. a pulse duration adjustment means or adjuster, of the device is provided for adjusting the pulse duration, for example between one of the aforementioned ranges.

The electrical stimulation or current or first and/or second currents may comprise an intensity or current amplitude, which is preferably selected or selectable to provide maximum contraction of the muscles being treated. By way of example, the intensity or amplitude may comprise approximately 10 mA, for example between 1 and 100 mA, such as between 5 and 50 mA, for example between 5 and 15 mA or between 7 and 25 mA, e.g. between 8 and 12 mA. The or a further adjustment means or adjuster, e.g. an intensity or amplitude adjustment means or adjuster, may be provided for adjusting the intensity or amplitude, for example from 0 to 500 mA or from 0 to 250 mA or from 0 to 200 mA or from 0 to 150 mA or from 0 to 100 mA.

In some embodiments, the apparatus is configured or programmed to provide the electrical stimulation or electric current or the first and/or second electric current for a predetermined period, which may comprise between 1 minute and 3 hours, say between 1 minute and 2.5, 2, 1.5 or 1 hour. In an embodiment, the apparatus is configured or programmed to provide the electrical stimulation or electric current for between, say, 5 and 30 minutes, preferably between 10 and 20 minutes. The or a further adjustment means or adjuster, e.g. a treatment duration adjustment means or adjuster, may be provided for adjusting the treatment duration, for example from 0 to 10 hours or from 0 to 5 hours or from 0 to 1 hour or from 0 to 30 minutes. The stimulation may be applied plural times a day, either with the same or different stimulation patterns. The apparatus may be programmable to apply stimulation one or more (e.g. plural) times a day. The apparatus may determine the time elapsed since the conclusion of a first or preceding stimulation session. The apparatus may not allow stimulation to be applied until a certain, known or pre-determined time period has elapsed. For example, when stimulation is required more than once a day, the apparatus may be operable to prevent the next stimulation session until a certain time period has elapsed.

The apparatus may be user programmable or programmable with control paradigms downloaded or downloadable from a host, for example a host computer, say via a wireless or wired connection.

The apparatus may comprise a control means, which may be programmed or programmable, for example to control one or more features of the electrical stimulation or current or currents, for example according to a predetermined treatment regime. The control means may comprise a control system and/or a controller and/or may comprise or be at least partially comprised in the electrical circuitry. The control means may comprise at least part of the adjustment means or adjuster, e.g. one or more of the frequency and/or pulse duration and/or intensity and/or amplitude and/or treatment duration adjustment means or adjusters.

The controller or control means may be operable to selectively energise the first, second and/or third electrode means, or combinations of the three, for example to provide lateral stimulation, vertical stimulation or a mixture of the two between two or more of the first, second and/or (if present) the third electrode means.

The connecting means may extend from the controller or control means. The connecting means may be removably or permanently connected to the controller or control means. The connecting means may comprise a unitary wired portion from which a pair of leads extends In some embodiments, the input means may be for or configured or operable to control and/or adjust one or more features of the electrical stimulation or electric current or the first and/or second electric current, for example the frequency and/or pulse duration and/or intensity and/or amplitude and/or treatment duration. Additionally or alternatively the device or input means may comprise an interface or connection means such as a connector or receptacle for connecting the device or control means to another device, such as a personal computer or a handheld device, which may be operable to program and/or control and/or adjust one or more of the aforementioned features.

The controller may be arranged to selectively energise the first and second electrode of the second electrode means and the first electrode means and/or the third electrode means with the same or different control paradigms. The control paradigms are selected from current, amplitude, frequency, pulse duration, pulse width, waveform, treatment duration, treatment periodicity, treatment time.

A further aspect of the invention provides a method or treatment regime, e.g. for training one or more muscles of the floor of the oral cavity, the method comprising providing or applying electrodes to a head, for example a face or external floor of mouth of a user laterally of the midline of the face of a user, and applying an electric current, laterally of the midline of the face.

The method may comprise stimulating one or more of the mylohyoid, geniohyoid and anterior belly of digastric muscles of the user. Preferably, by applying the electric current for sufficient time the position of the hyoid and hypopharyngeal airway will be changed, thereby to reduce SBD and, preferably OSA.

The apparatus or control means or adjustment means may be configured or programmed to control one or more features of the electrical stimulation or electric current or the first and/or second electric current, for example in a predetermined manner and/or according to a predetermined treatment regime. The device or control means may be operable or programmable to create and/or alter the predetermined treatment regime, for example by a device to which the electrical stimulation device is connected, e.g. via the input means.

Another aspect of the invention provides a computer program element comprising computer readable program code means for causing a processor to execute a procedure to implement a method or treatment regime comprising providing electrical stimulation to one or more oral muscles, e.g. palate and/or tongue muscles, through the lining of the mouth, for example the oral mucosa, e.g. to increase resting muscle tone and/or muscle tone during sleep.

Another aspect of the invention provides a method or treatment regime, e.g. for training one or more oral muscles such as by trans mucosal neuromuscular electrical stimulation, the method comprising providing or applying electrical stimulation to one or more oral muscles, e.g. palate and/or tongue muscles, through the lining of the mouth, for example the oral mucosa, e.g. to increase resting muscle tone and/or muscle tone during sleep.

A yet further aspect of the invention comprises a device for apparatus for training one or more oral muscles, for example a trans mucosal neuromuscular electrical stimulation device, the device comprising a mouthpiece having a pair of arms joined at a proximal end of each and diverging towards a distal end of each, at least one arm having a flange extending therefrom and defining a flat surface, the flange carrying at least one electrode which stands proud from the flat surface.

In embodiments both arms have at least one flange. Each flange may have at least one electrode. One or more of the electrodes may stand proud of the surrounding flange area.

For the avoidance of doubt, any of the features described herein apply equally to any aspect of the invention.

The method or treatment regime may comprise providing or applying a current, for example an electric current or impulse current, such as a biphasic electric current or impulse current, e.g. to the one or more oral muscles.

Another aspect of the invention provides a method or treatment regime, e.g. for training one or more muscles of the floor of the oral cavity, the method comprising providing or applying electrodes to a head of a user laterally of the midline of the face or external floor of mouth of a user, and applying an electric current, laterally of the midline of the face.

The method or treatment regime may comprise providing or applying a first current and/or a second current, which second current may be different from the first current. The current or at least one, e.g. both, of the first and/or second current may comprise an alternating current. The or at least one of the or each current may comprise a frequency of between 1 and 150 Hz, for example between 10 and 140 Hz, e.g. between 15 and 130 Hz, preferably between 20 and 120 Hz, more preferably between 20 and 50 Hz and/or between 50 and 120 Hz. In some embodiments, the first current comprises a frequency of between 20 and 50 Hz and/or the second current comprises a frequency of between 50 and 120 Hz.

In embodiments, phases of the biphasic current, or the first and second currents, may be applied simultaneously and/or concurrently. In some embodiments, phases of the biphasic current, or the first and second currents, may be applied in series and/or in sequence and/or in succession.

The current or at least one, e.g. both, of the first and/or second current may comprise an impulse current. The pulse duration of the or each impulse current may be between 50 and 1000 μs, for example between 100 and 900 μs, e.g. between 150 and 800 μs, preferably between 200 and 700 μs.

The electrical stimulation or current or first and/or second currents may comprise an intensity or current amplitude, which is preferably selected or selectable to provide maximum contraction of the muscles being treated. By way of example, the intensity or amplitude may comprise approximately 10 mA, for example between 1 and 100 mA, such as between 5 and 50 mA, for example between 5 and 15 mA or between 7 and 25 mA, e.g. between 8 and 12 mA.

The method or treatment regime may comprise providing or applying the electrical stimulation or electric current or the first and/or second electric current for a predetermined period, which may comprise between 1 minute and 3 hours, for example between 5 and 30 minutes, preferably between 10 and 20 minutes.

The electrical stimulation may be applied in one or more than one stimulation sessions per day. The more than on stimulation sessions per day may be the same or different.

In some embodiments, the method or treatment regime may comprise providing or applying the electrical stimulation or electric current or the first and/or second electric current for a first predetermined period to a first muscle or group of muscles and/or to an upper or dorsal surface of the tongue. The first muscle or group of muscles may include one or more palate and/or tongue muscles, e.g. one or more of the intrinsic surface muscles, the uvular muscle, the levator veli palatini muscle and the palatopharyngeus muscle.

Additionally or alternatively, the method or treatment regime may comprise providing or applying the electrical stimulation or electric current or the first and/or second electric current for a second predetermined period to a second muscle or group of muscles and/or to the underside of the tongue, e.g. sublingually. The second muscle or group of muscles may include one or more palate and/or tongue muscles, one or more of which may be different from the first muscle or group of muscles e.g. the genioglossus muscle. By way of example, the first predetermined period may comprise between 1 minute and 3 hours, for example between five and thirty minutes, for example five or ten or fifteen or twenty or thirty minutes and/or the second predetermined period may comprise between five and thirty minutes, for example five or ten or fifteen or twenty or thirty minutes.

Additionally or alternatively, the method or treatment regime comprises carrying out one or more of the aforementioned steps at predetermined intervals, which may comprise between one and ten times per day or any number therebetween, for example twice per day. Additionally or alternatively, the method or treatment regime comprises carrying out one or more of the aforementioned steps over a predetermined treatment period, which may comprise between one and twelve weeks, for example between two and ten weeks, e.g. between five and eight weeks, such as six weeks.

The method or treatment regime may comprise adjusting one or more features of the electrical stimulation or electric current or the first and/or second electric current, for example the frequency and/or pulse duration and/or intensity and/or amplitude and/or treatment duration. The adjustment may be carried out using an input means, such as one or more push buttons and/or dials or the like or via an interface or connection means such as a connector or receptacle by a device, such as a personal computer, smartphone, tablet or other personal computing device or a handheld device. Advantageously, software held on a computing device may be operable to control or to program the apparatus with a command set.

In some embodiments, the method or treatment regime comprises a first, e.g. treatment, period, for example during which the electrical stimulation or electric current or the first and/or second electric current is or are provided or applied, e.g. to build resting muscle tone and/or muscle tone during sleep. The method or treatment regime may also comprise a second, e.g. maintenance, period, for example during which one or more features of the electrical stimulation or electric current or the first and/or second electric current is adjusted or changed, e.g. with respect to the first period, e.g. to maintain resting muscle tone and/or muscle tone during sleep. The first period may comprise a first regime and/or the second period may comprise a second regime, e.g. different from the first regime.

In an exemplary embodiment, the method or treatment regime comprises providing or applying electrical stimulation to the one or more oral muscles for 10 to 20 minutes, twice per day for six weeks, for example to build resting muscle tone and/or muscle tone during sleep. Additionally or alternatively, the method or treatment regime may comprise providing or applying electrical stimulation to the one or more oral muscles for 10 to 20 minutes, once per day on an ongoing basis, for example to maintain resting muscle tone and/or muscle tone during sleep.

Another aspect of the invention provides a method or treatment regime, e.g. for training one or more oral muscles such as by sensory stimulation, the method comprising providing or applying a vibratory stimulation to one or more oral muscles, e.g. palate and/or tongue muscles and/or muscles of the floor of the mouth. The method may further comprise any one or more features of the method described above.

A further aspect of the invention provides a computer program element comprising computer readable program code means for causing a processor to execute a procedure to implement the aforementioned method or treatment regime. A yet further aspect of the invention provides the computer program element embodied on a computer readable medium.

A yet further aspect of the invention provides a computer readable medium having a program stored thereon, where the program is arranged to make a computer execute a procedure to implement the aforementioned method or treatment regime.

A yet further aspect of the invention provides a control means or control system or controller comprising the aforementioned computer program element or computer readable medium or for controlling a treatment regime to train one or more oral muscles, such as by trans mucosal neuromuscular electrical stimulation, for example for controlling the method described above.

Within the scope of this application it is expressly envisaged that the various aspects, embodiments, examples and alternatives set out in the preceding paragraphs, in the claims and/or in the following description and drawings, and in particular the individual features thereof, may be taken independently or in any combination. Features described in connection with one aspect or embodiment of the invention are applicable to all aspects or embodiments, unless such features are incompatible.

Embodiments of the invention will now be described by way of example only with reference to the accompanying drawings in which:

FIG. 5 is a schematic of a human mouth showing the palatoglossus and surface of the tongue;

FIG. 6 is a schematic illustrating the extrinsic tongue muscles of a human tongue;

FIG. 7 is a schematic illustrating the intrinsic tongue muscles of a human tongue;

FIG. 8 is another schematic of a human mouth showing the muscles of the palate;

FIG. 9 is a schematic illustrating further muscles of the palate; and

FIGS. 10A to 10D are diagrammatic representations of non-limiting sets of possible actuation modes.

Figure 1:
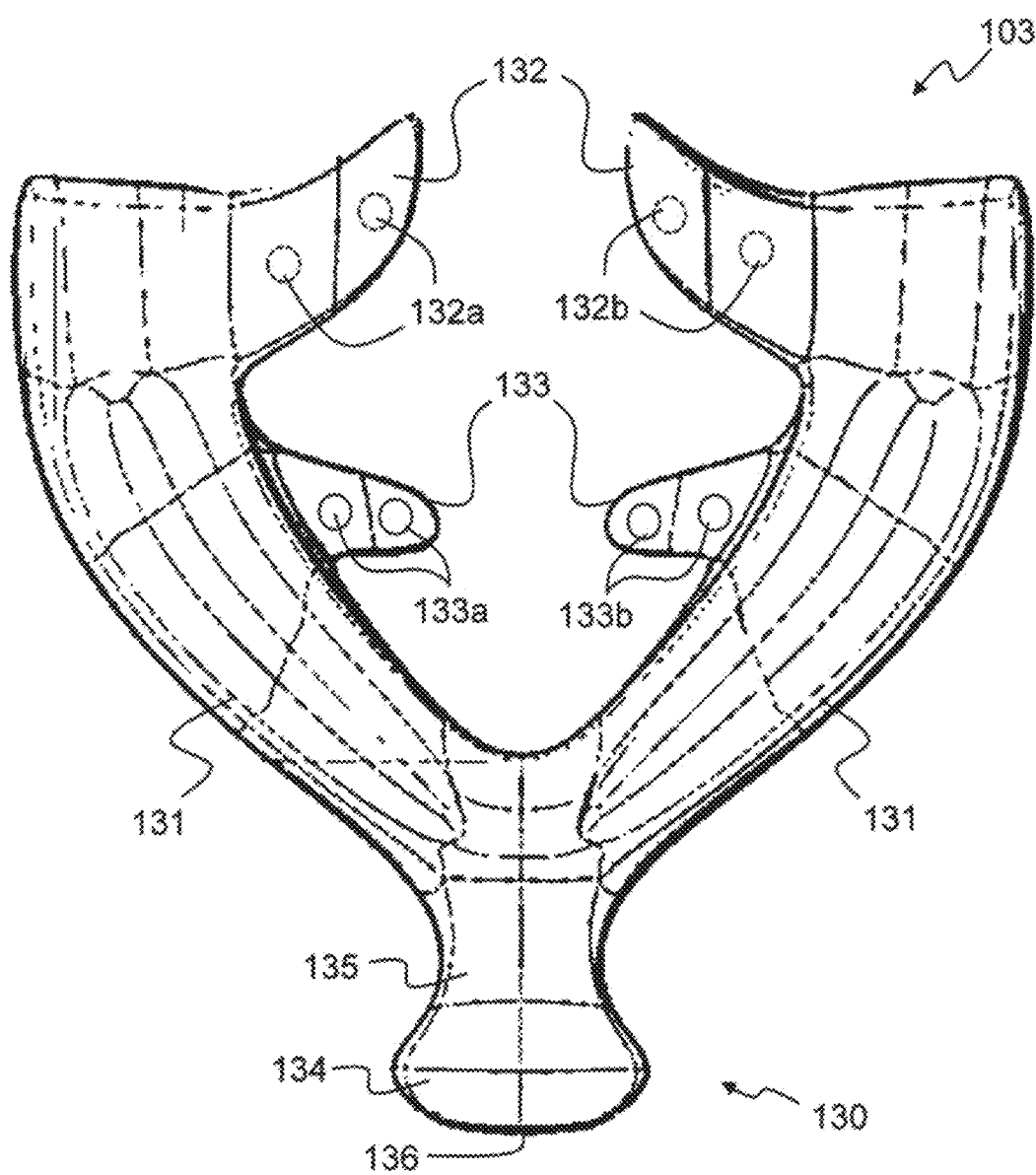
FIG. 1 is a plan view of a part of apparatus according to an embodiment of the invention.
Figure 2:
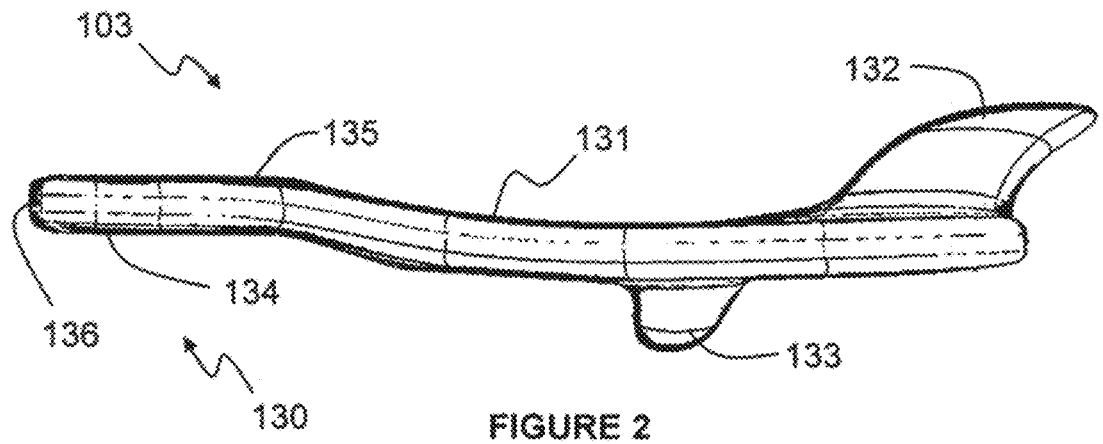
FIG. 2 is a side elevation of the of FIG. 1.

Referring now to FIGS. 1 and 2, there is a shown a component of the apparatus according to the invention. The FIGS. 1 and 2 show a mouthpiece 103 which includes a gripping base 130 and a pair of curved arms 131 formed integrally with one end of the base 130 to form a horseshoe shape. Each of the arms has first and second contact flanges 132, 133 within which are provided (or upon which are located) electrodes (132a, b; 133a, b).

The first contact flanges 132 extend inwardly toward one another from the free end of a respective one of the arms 131 and upwardly to form a curved shape for accommodating the dorsal tongue surface 57 of a tongue of a patient (not shown). The second contact flanges 133 extend inwardly toward one another from an intermediate part of a respective one of the arms 131 and downwardly to form a curved shape for accommodating the sublingual tongue surface. As looked at from the side (FIG. 2), the electrode or electrodes 132a on the first contact flanges 132 will face downwardly whereas those electrodes 133a, 133b on the second contact flanges 133 will face upwardly. In this way, with the user's tongue located between the first 132 and second 133 contact flanges the electrodes 132a, 132b; 133a, 133b are able to apply an electrical field in a vertical direction and will specifically target the genioglossus muscle.

The base 130 includes an enlarged end 134 joined to the arms 131 by a necked portion 135. The end surface of the enlarged end 134 includes an electrical connector 136 for connection with a source of power (not shown). The connector 136 may comprise a USB, microUSB, USB-C, FireWire®, Thuderbolt®, magnetic connectors or any other suitable type of wired connector. In other embodiments, the connector is replaced with a wireless connection means. In some embodiments, the mouthpiece incorporates a power source, such as a battery.

The mouthpiece 103 also includes electrical circuitry (not shown) communicating with the respective series of electrodes 132a, 132b, 133a, 133b at each surface of each flange 132, 133, that is to say each of the upper and lower surfaces of each of the flanges 132, 133. Each of these electrode series 132a, 132b; 133a, 133b is electrically isolated from the others by a shielding material, thereby enabling all surrounding muscles to be stimulated simultaneously or in any sequence required. The electrodes 132a, 132b; 133a, 133b cooperate with the outer surface of the flanges 132, 133 with which they are associated to form a substantially contiguous surface. In this embodiment, the mouthpiece 103 is formed of a food grade or a biocompatible grade plastic material, for example made from silicone plastics material. The electrodes 132a, 132b; 133a, 133b in this embodiment are preferably formed of metal, for example gold, silver or copper or composite material or any such alloy with an exposed surface.

In use, the mouthpiece 103 is placed in a patient's mouth and the tongue of the patient is received within the mouthpiece 103 such that the dorsal tongue surface 57 is in contact with the first contact flanges 132 and the sublingual tongue surface is in contact with the second contact flanges 133. It will be appreciated by those skilled in the art that the first flanges 132 will contact a rearward or posterior portion of the dorsal tongue surface 57 and the second flanges 133 will contact a frontward or anterior portion of the sublingual tongue surface. With the patient's mouth closed, the flanges 132, 133 are also able to contact and stimulate adjacent muscles on the other side of the tongue, for example the palate muscles. The mouthpiece 103 enables the muscles to be stimulated on both sides of the tongue sequentially or simultaneously. It will be appreciated that with this design, the muscles based in and around the tongue may be stimulated, including those in hard and soft palate areas.

Figure 3A:
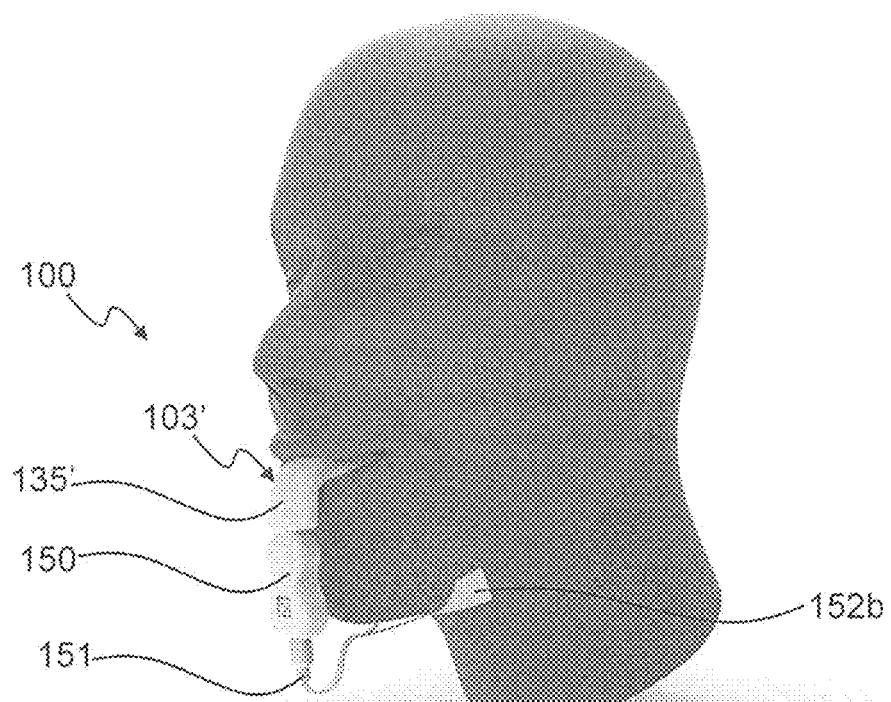
FIG. 3A is an elevation of a user using the apparatus of the invention.
Figure 3B:
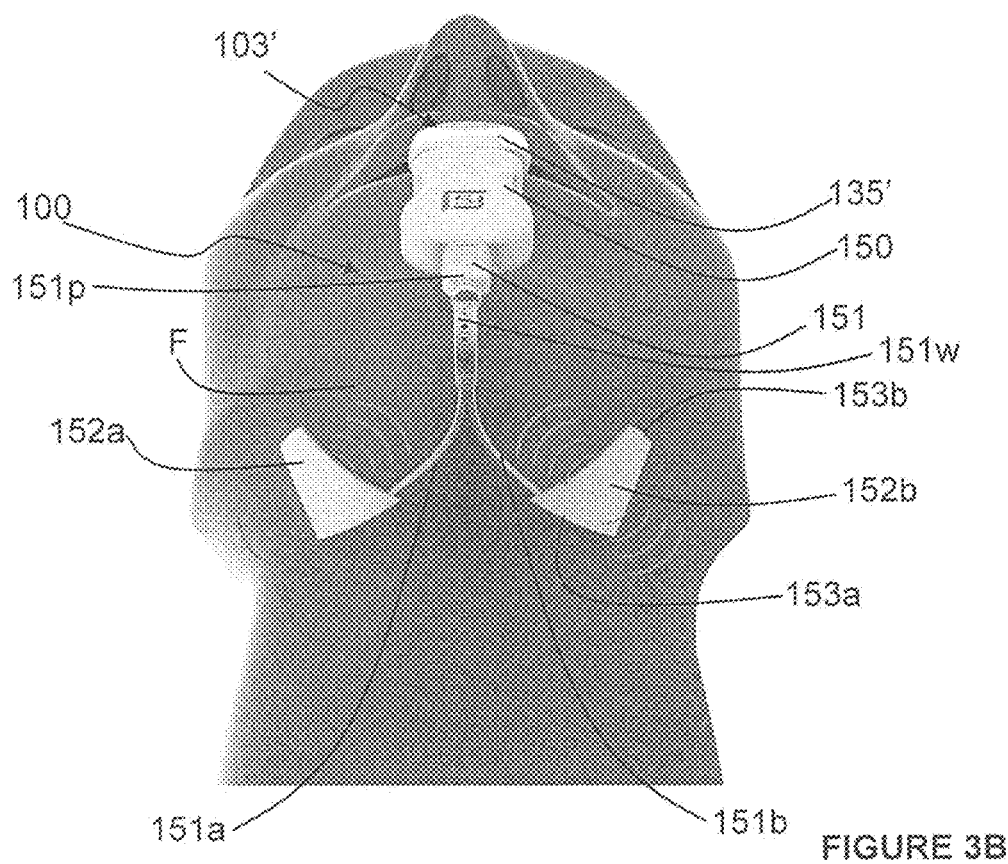
FIG. 3B is a view from below of a user using the apparatus of the invention.
Figure 4A:
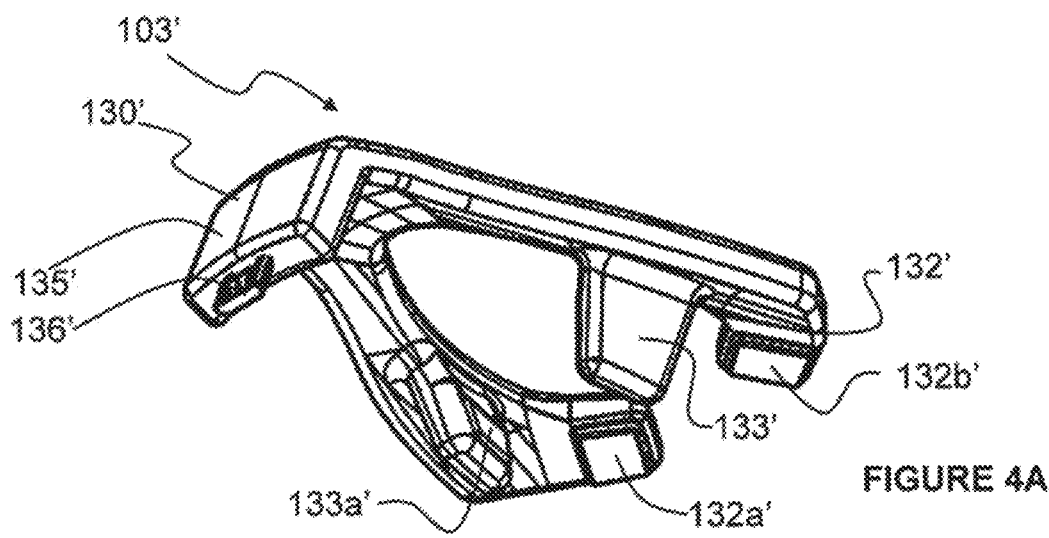
FIGS. 4A, 4B and 4C are respectively perspective, plan and side elevation views of a part of the apparatus of FIGS. 3A and 3B.
Figure 4B:
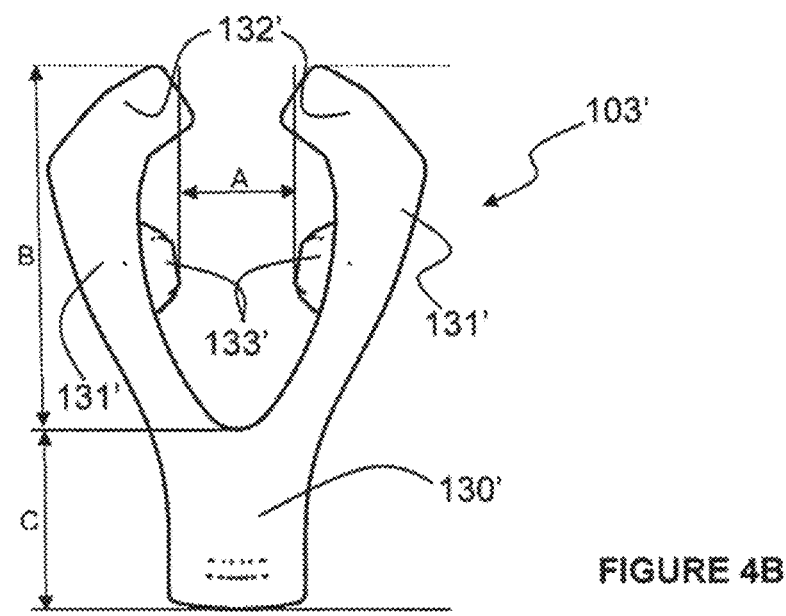
Figure 4C:
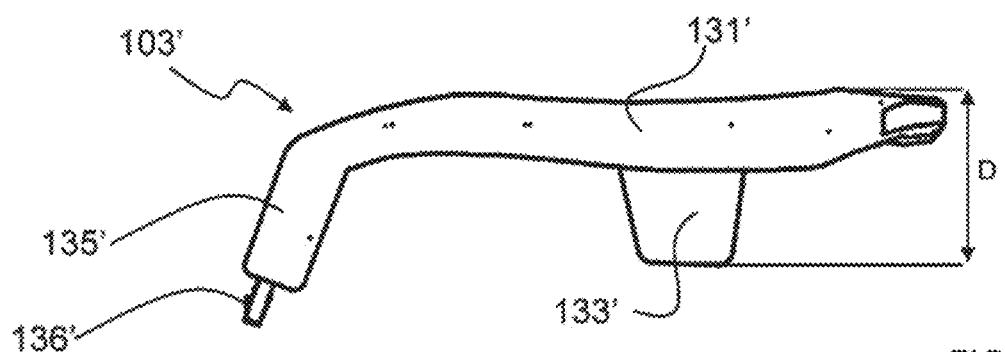

Referring now to FIGS. 3A and 3B there is shown apparatus 100 according to the invention comprising a mouthpiece 103' located within the mouth of a user. The mouthpiece 103' is similar to that shown in FIGS. 1 and 2 (and uses the same numerals to indicate the equivalent components but distinguished by a prime (')) and is shown in FIGS. 4A to 4C. The mouthpiece 103' has a gripping base 130' which has an extended and depending portion 135' which extends over a user's bottom lip.

The terminal portion of the depending portion 130' has an interface 136' for engaging with a control and/or power unit 150 which is arranged to provide the power to the electrodes 132a', 132b', 133a', 133b' of the mouthpiece 103' and to further electrodes. It is noted that the electrodes 132a', 132b', 133a', 133b' of the mouthpiece 103' are shown as single pads, although they could be multiple pads or contact points. We prefer a single pad as it provides a large surface area. The electrodes 132a', 132b', 133a', 133b' of the mouthpiece 103' protrude proud of the adjacent portions of the associated flanges 132', 133' to facilitate a good connection with the facing portion of the user's tongue.

The apparatus 100 further comprises a wired connection 151 from the control unit 150 to a pair of shaped electrodes 152a, 152b. The wired connection 151 may be permanently wired to the controller 150 or may comprise a plug 151a (or a socket) for engagement with a socket (or a plug) (not shown) located on the controller 150. The wired connection 151 includes a unitary wired portion 151b from which a pair of leads 151a, 151b extends. The pair of leads 151a, 151b connect the control unit 150 to the pair of shaped electrodes 152a, 152b. That is, the first of the pair of leads 151a connects the control unit 150 to the first of the pair of shaped electrodes 152a, and the second of the pair of leads 151b connects the control unit 150 to the second of the pair of shaped electrodes 152b. Each of the electrodes 152a, 152b is mounted on or in a body of concave planar shape having a quadrilateral perimeter with a relatively wide proximal portion 153a for location at the posterior of the external floor of the user's mouth F and a relatively narrow distal portion 153b for location at or towards an anterior portion of the external floor of the user's mouth. The shaped electrodes 152a, 152b are sufficiently concave to follow the facing surface of the user's chin, or at least to be able to comfortably follow the facing surface of the user's chin and jaw line (as seen in FIG. 3A).

In use, the electrodes 152a, 152b are secured to the external floor or the mouth of the user F, underneath the chin, lateral of the midline of the user's face or external floor of mouth using a medically acceptable adhesive, which is readily removable from the electrodes 152a, 152b and the user. Alternatively, the electrodes 152a, 152b can bear an adhesive which is re-usable. Advantageously, the pair of leads 151a, 151b are the same length, which enables the electrodes 152a, 152b to be located or locatable lateral of a midline of the face of the user in a symmetrical fashion.

In order to train the muscles of the mouth, the control unit 150 is programmed (or a pre-programmed program is selected) and the mouthpiece 103' and electrodes 152a, 152b are connected to the control unit 150. Once the program has started, the control unit 150 will energise the electrodes according to the required or desired actuation profile to apply the electrical signal to the muscles.

Beneficially, the electrodes 152a, 152b will apply an electrical signal to the muscles of the floor of the mouth, namely one or more of the mylohyoid, geniohyoid and anterior belly of digastric muscles whilst those of the mouthpiece 103' will apply an electrical signal to the genioglossus muscle and the body of the tongue.

The controller 150 may be operable to energise the electrodes sequentially and/or simultaneously to provide various current modes to the muscles of the mouth. For example, the first, second and third electrodes could be energised to cause lateral stimulation, vertical stimulation or diagonal stimulation, or mixtures of the same. A (non-limiting) set of possible actuation modes are shown diagrammatically in FIGS. 10A to 10D. The controller 150 may be programmed or programmable to cause various modes of operation. In other embodiments the actuation modes may be entirely diagonal or may be mixed, for example:
1) vertical (132-133),
   lateral (133a-133b),
   diagonal (152a-133b and 152b-133a),
2) diagonal (132a-133b, 132b-133a),
   lateral (133a-133b)
   vertical (152a-133a and 152b-133b)
3) lateral (132a-132b)
   diagonal (132a-133b, 132b-133a)
   lateral (133a-133b)
   vertical (152a-133a and 152b-133b)

The particular modes of operation are selected according to the requirements of the user. The controller 150 may be arranged to change modes of actuation, for example the controller may cycle through various modes during a period of operation. This may be achieved by changing the polarity of the electrodes.

The control unit 150 may comprise batteries (not shown) and logic and control circuitry (not shown) to control the application of electric currents to the various electrodes.

Turning now to FIGS. 5 to 9, there is shown various tongue and palate muscles. Features of the mouth shown in FIGS. 5 to 7 illustrate more clearly the tongue muscles, wherein there is shown the pharyngopalatine arch 51, palatine tonsil 52, palatoglossus 53, buccinator 54, valate papillae 55, fungiform papillae 56, dorsal tongue surface 57, styloglossus 58, hyoglossus 59, mandible bone 60, genioglossus 61, longitudinal, transverse and vertical intrinsic muscles 62, 63, 64 and geniohyoid 65.

It is well established that the tone of the genioglossus muscle 61 most affects the collapsibility of the tongue as it is the biggest of the extrinsic muscle and responsible for pulling the tongue forward and increasing the airway opening in the throat. The tone of intrinsic surface muscles, such as the longitudinal and transverse intrinsic muscles 62, 63, also contribute to the reduction of the collapsibility of the airway.

Features of the mouth shown in FIGS. 8 and 9 illustrate more clearly the palate muscles, wherein there is shown the dental arch 66, premaxilla 67, incisive foramen 68, palatine process of maxilla 69, palatine bone 70, posterior nasal spine 71, palatine foramen 72, hamulus 73, tensor palatini muscle 74, levator veli palatini muscle 75, tensor veli palatini muscle 76, uvular muscle 77 and palatopharyngeus muscle 78.

To a varying degree, the constrictor and dilator muscles of the palate also contribute to snoring and sleep apnoea. The aim of the treatment is to dilate the throat, hence electrical stimulation is directed at the dilatory palate muscles in the midline, such as the uvular muscle 77, the levator veli palatini muscle 75 and the palatopharyngeus muscle 78.

We have now found that the muscles of the floor of the mouth, and specifically one or more of mylohyoid, geniohyoid and anterior belly of digastric muscles also have an effect on the incidence of sleep apnoea, snoring and SDB in general. We have fund that lateral application of an electrical current across the chin is able to strengthen the muscles of the floor of the mouth which has a surprising and positive effect on muscle tone and helps to further reduce the incidence of SBDs. Indeed, we have found that toning the mylohyoid, and geniohyoid muscles improves the position of the hyoid and hypopharyngeal airway, thereby significantly reducing the incidence of OSA, snoring and SDB in general.

In use, the mouthpiece 103' is applied to the dorsal tongue surface 57 and/or the sublingual surface and current, for example biphasic currents are applied, each of which may be configured with a first set of parameters including intensity, frequency and pulse duration. The parameters are selected to provide maximal contraction of these muscles in the user and the treatment is carried out for a period of 20 minutes.

The intensity, frequency and pulse duration may then be adjusted and the mouthpiece 103' is applied to the underside of the tongue and/or the dorsal surface 57. The two currents, for example the two biphasic currents, now having a second set of parameters, are applied and transmitted trans mucosally to stimulate the genioglossus muscle 61. The second set of parameters are selected to provide maximal contraction of the user's genioglossus muscle 61 and the treatment is carried out for a period of, say, up to 3 hours, for example 20 to 30 minutes.

The application of currents, e.g. biphasic currents, according to the parameters described above stimulate the aforementioned skeletal muscles. It is also believed that the application of this biphasic current to these skeletal muscles creates a further, sensory function, such as a vibratory sensation. Whilst not wishing to be bound by any theory, it is believed that this electrical and vibratory stimulation of the nerves provides feed back to the brain which further enhances the improvement in muscle tone. Specifically, it is believed that the effectiveness of this treatment is enhanced by multisensory integration within the nervous system.

The current applied to the electrodes 152a, 152b may be the same or different to that applied by the mouthpiece 103'.

For example, the controller 150 may be arranged to selectively energise the electrodes 152a, 152b laterally with a current having a first set of parameters (mode 1). This mode 1 may be stopped or continued whilst the controller 150 is arranged to selectively energised, say electrodes 133a', 133b' and electrodes 132a' and 132b' vertically with a second set of parameters (mode 2). Additionally or alternatively, the controller 150 may be arranged to energise electrodes 152a, 152b and electrodes 133a', 133b' vertically with a third set of parameters (mode 3). Mode 3 may be arrested or continued whilst the controller is arranged to energise electrodes 132a', 132b' laterally with a fourth set of parameters (mode 4). As will be appreciated, different and further modes may be provided based on the combination of the six separately controllable electrodes, for example to generate lateral or vertical stimulation.

The first, second, third or fourth (or nth) set of parameters may all be the same or different. Some may be the same whilst some are different.

By way of example, a treatment regime could involve a say six-week induction period during which each of the aforementioned muscle groups are stimulated for a period of 10 to 30 minutes, twice daily. The treatment regime, which is designed to build muscle tone, could then be followed by an ongoing maintenance regime involving 10 to 20 minute sessions once per day.

The apparatus 100 may be operable to adjust the current amplitude of a first current, e.g. first biphasic or monophasic current, from 0 to 100 mA. The apparatus 100 may be operable to adjust the current amplitude of, for example, a second biphasic current from 0 to 100 mA. The apparatus 100 may be operable to adjust the duration of the period during which the first current, e.g. biphasic current, is supplied from say 1 to 30 minutes. The apparatus 100 may be operable to adjust the duration of the period during which the second current, e.g. biphasic or monophasic current, is supplied from say 1 to 30 minutes. The apparatus 100 may be operable to energise only the external electrodes 152a, 153a or some or all of the mouthpiece electrodes 132a, 132b; 133a, 133b, or both or all at the same time.

A USB port or other interface may be provided and configured to enable the device 103, 103' to be connected to a personal computer (not shown) to program one or more characteristics of the first and second currents, e.g. biphasic or monophasic currents, independently. In an embodiment, the frequency of the first current, e.g. biphasic current, is set at a value between say 1 and 150 Hz, for example between 2 and 50 Hz, the second current, e.g. second monophasic current, is set at a value between 3 and 120 Hz and the pulse duration of each current, e.g. biphasic or monophasic current, may be set at a value between 200 and 700 µs. The personal computer, tablet, smartphone or other hand-held computing device (not shown) may also incorporate control software operable to override any, say, dials or buttons or other user interface on the control body 150. The software may be programmed to apply currents, e.g. biphasic or monophasic currents, having predetermined characteristics independent from one another, such as amplitudes, frequencies and pulse durations and for a predetermined period of time. It is further envisaged that the device 103, 103' could incorporate a memory on which is stored such predetermined characteristics, which may be modified by connecting a personal computer or so on (not shown) to the device 103, 103' via the USB port or other interface. In such embodiments, the dials may be omitted or configured to adjust the aforementioned characteristics from their pre-programmed values. In some embodiments, it is envisaged that more or less functionality is provided by manual dials, buttons and the like.

The apparatus may have protection built into the hardware at multiple levels and firmware which protects the user and hardware from malfunctioning or tampering. If a malfunction (or tampering) is detected the apparatus will preferably enter a 'safe state' and automatically arrest any current and future stimulation unless and until the malfunction etc. has been addressed. Malfunction detection may detect an abnormal operating parameter of the apparatus and may also include abnormal environmental conditions of the apparatus.

It will be appreciated by those skilled in the art that several variations to the aforementioned embodiments are envisaged without departing from the scope of the invention.

For example, the mouthpiece 103, 103' may take any suitable form, but is preferably designed to enable the electrical stimulation to be applied to the appropriate muscles as described above. The output of the control body may be varied by changing dials on the body itself or it may be altered by interfacing the control body 150 with, for example software, such as an APP held on a mobile device, such as a personal computer, smart phone or tablet. The software may be programmed to apply desired or required currents, for example biphasic currents, having predetermined characteristics (current, duration, frequency) independent from one another, such as amplitudes, frequencies and pulse durations and for a predetermined period of time. It is further envisaged that the apparatus 100 could incorporate a memory on which is stored such predetermined characteristics, which may be modified by connecting a personal computer (not shown) to the apparatus 100 via a USB port or other interface connection. Other interface connections include wired and wireless connections, for example Bluetooth®, IR, NFC Wi-Fi and so on.

The controller and/or the APP may be operable to only control a pre-registered mouthpiece and/or pre-registered external electrodes. The mouthpiece may be provided with a serial number, code or other unique identifier so that the controller and/or the APP and mouthpiece can be uniquely linked to avoid a mouthpiece being used with another's controller and/or APP and vice versa. The external electrodes may be provided with a serial number, code or other unique identifier so that the controller and/or APP and external electrodes can be uniquely linked to avoid external electrodes being used with another's controller and/or APP and vice versa. The controller and/or APP may be operable to associate a particular mouthpiece with a particular set of external electrodes so that a particular mouthpiece can only be used with a particular set of external electrodes.

It will also be appreciated by those skilled in the art that any number of combinations of the aforementioned features and/or those shown in the appended drawings provide clear advantages over the prior art and are therefore within the scope of the invention described herein.

The invention claimed is:

1. An apparatus for training oral muscle tone of an awake user, the apparatus comprising a mouthpiece having a first electrode set associated with the mouthpiece and an external electrode set for location exterior of the mouth of the awake user, electrical circuitry operatively connected to the first electrode set and the external electrode set, wherein a controller configured to selectively energize one or both of the first electrode set and the external electrode set according to a treatment regime selected by the awake user, wherein the controller is operably connected the first electrode set and the external electrode set, wherein the apparatus is configured to provide, in use, via the first electrode set and/or the external electrode set, electrical stimulation to one or more oral muscles to increase resting muscle tone and/or muscle tone during sleep, the external electrode set comprising a first and second electrode being located or locatable lateral of a midline of a face of the awake user and wherein the controller is configured to apply electrical current laterally between electrodes of the first electrode set on a first side of a midline of the user's face in a first mode and to apply electrical current vertically between an electrode of the first electrode set and an electrode of the external electrode set that is on the same side of the midline of the user's face as the electrode of the first electrode set in a second mode.

2. The apparatus according to claim 1, wherein the controller is further configured to apply an electric current laterally between the first and second electrodes of the external electrode in a third mode.

3. The apparatus according to claim 1, wherein the first and second electrodes are mounted on or in planar concave bodies.

4. The apparatus according to claim 1, wherein the first electrode set is associated with first contact flanges extending from one or more arms of the mouthpiece.

5. The apparatus according to claim 1, wherein the first electrode set comprises a first electrode and a second electrode of the first electrode set and are located or locatable lateral of the midline of the face or external floor of mouth of the awake user.

6. The apparatus according to claim 1, wherein the mouthpiece comprises arms each joined at a proximal end, wherein each of the arms comprise a first and second contact flange extending therefrom.

7. The apparatus according to claim 6, wherein the first electrode set is associated with the first contact flanges, wherein the first contract flanges are configured to contact a sublingual surface of the awake user.

8. The apparatus according to claim 7, wherein the controller is arranged to selectively energize the first electrode set, the second electrode set and/or a third electrode set associated with the second contact flanges according to the predetermined treatment regime selected by the awake user.

9. The apparatus according to claim 1, wherein the controller comprises a user interface and is configured to selectively choose between the first mode and the second mode and/or and select different control paradigms.

10. The apparatus according to claim 9, wherein the control paradigms are selected from current, amplitude, frequency, pulse duration, pulse width, waveform, treatment duration, treatment periodicity, treatment time.

11. An apparatus for training oral muscle tone of an awake user, the apparatus comprising
a first electrode set comprising first contact flanges each having an electrode configured to be on a first side of a midline of the user's face when worn, and a second electrode set comprising second contact flanges each having an electrode configured to be on a second side of a midline of the user's face when worn, wherein the first contact flanges and the second contact flanges extend from one or more arms of a mouthpiece,
an external electrode set having a pair of electrodes locatable on an external surface of a floor of a mouth of the awake user wherein the first and second electrode sets are configured to provide electrical current to oral mucosa, wherein the external electrode set comprises a first electrode and a second electrode and is configured to provide electrical current across the midline of user's face when worn,
a controller configured to apply electrical current laterally between electrodes of the first electrode set on a first side of a midline of the user's face in a first mode and to apply electrical current vertically between an electrode of the first electrode set and an electrode of the external electrode set that is on the same side of the midline of the user's face as the electrode of the first electrode set in a second mode.

12. The apparatus according to claim 11, wherein the mouthpiece comprises a gripping base configured to extend over the awake user's lip.

13. The apparatus according to claim 11, wherein the controller comprises a user interface and is configured to selectively energize the first, second, and/or the external electrode set according to selectable control paradigms.

14. The apparatus according to claim 1, wherein the controller is configured to energize the first electrode and external electrode set according to one or more selectable control paradigms.

15. The apparatus according to claim 12, further comprising electrical circuitry between said mouthpiece, said first electrode set, said second electrode set and said external electrode set.

16. A method or treatment regime for training one or more muscles of a floor of an oral cavity during an awake state of a user including the mylohyoid, geniohyoid and anterior belly of the digastric muscles, the method comprising applying electric current in a first mode vertically between a first electrode of an external electrode set and a first electrode of a second electrode set that are both on a first side of a midline of the user's face or external floor of a mouth of the user, and applying electric current in a second mode laterally between the first electrode and the second electrode of the second electrode set that is associated with a mouthpiece, and selecting a mode of operation via a controller operably connected to the external electrode set and the second electrode set, wherein applying the electric current via the external electrode set and the second electrode set is performed while the user is awake.

17. The method according to claim 16, comprising applying electrical current to a third electrode set operably connected to the controller, wherein the third electrode set is associated with the mouthpiece.

18. The method according to claim 16, comprising applying the electric current for a predetermined period of time in an awake state to increase muscle tone during sleep.

19. The method of claim 16, comprising adjusting a control paradigm via the controller, control paradigm is configured to be adjusted by the user.

20. The apparatus according to claim 1, wherein the treatment regime is configured to be adjusted by the awake user.

21. The apparatus of claim 1, wherein the controller is configured to apply different parameters for the electrical current applied in the first mode as compared to the second mode.

* * * * *